United States Patent [19]

Hosoda

[11] Patent Number: 5,569,268
[45] Date of Patent: Oct. 29, 1996

[54] ENDOSCOPIC INSTRUMENT FOR LIGATING VARIX

[75] Inventor: Masayuki Hosoda, Tokyo, Japan

[73] Assignee: Kabushiki Kaisha Top, Tokyo, Japan

[21] Appl. No.: 388,816

[22] Filed: Feb. 15, 1995

[30] Foreign Application Priority Data

Apr. 26, 1994 [JP] Japan ..................... 6-088893

[51] Int. Cl.⁶ .................................................. A61B 17/00
[52] U.S. Cl. ............................................ 606/140; 606/139
[58] Field of Search .................................. 606/140, 141, 606/139, 135, 165

[56] References Cited

U.S. PATENT DOCUMENTS

| | | | |
|---|---|---|---|
| 4,493,319 | 1/1985 | Polk et al. | 606/141 |
| 4,735,194 | 4/1988 | Stiegmann . | |
| 5,269,789 | 12/1993 | Chin et al. . | |
| 5,320,630 | 6/1994 | Ahmed | 606/140 |
| 5,356,416 | 10/1994 | Chu et al. | 606/140 |

FOREIGN PATENT DOCUMENTS 759786  7/1995  Japan .

Primary Examiner—Michael Powell Buiz
Assistant Examiner—Jeffrey A. Schmidt
Attorney, Agent, or Firm—Birch, Stewart, Kolasch & Birch, LLP

[57] ABSTRACT

An endoscopic ligating instrument has an outer tube having a rear end in which the tip end of an endoscope is mounted. An inner tube with a trip wire connected thereto is axially movably inserted in the outer tube. When the inner tube is moved rearwardly, the inner tube is urged to move forwardly by a spring. Three ligating O-rings are mounted respectively at axially equally spaced positions on the outer circumferential surface of a portion of the inner tube which projects from the outer tube. Four arms extending forwardly from the outer tube are disposed respectively at circumferentially equally spaced positions over the outer circumferential surface of the inner tube. Each of the arms has teeth disposed behind the ligating O-rings, respectively, and having front pushing surfaces for pushing the ligating O-rings forwardly when the inner tube is moved rearwardly and rear slant surfaces for riding over the ligating O-rings and spreading the arms radially outwardly when the inner tube is moved forwardly. The endoscopic ligating instrument can ligate a plurality of varices successively which the endoscope is being inserted in a cavity in the body of a patient.

12 Claims, 7 Drawing Sheets

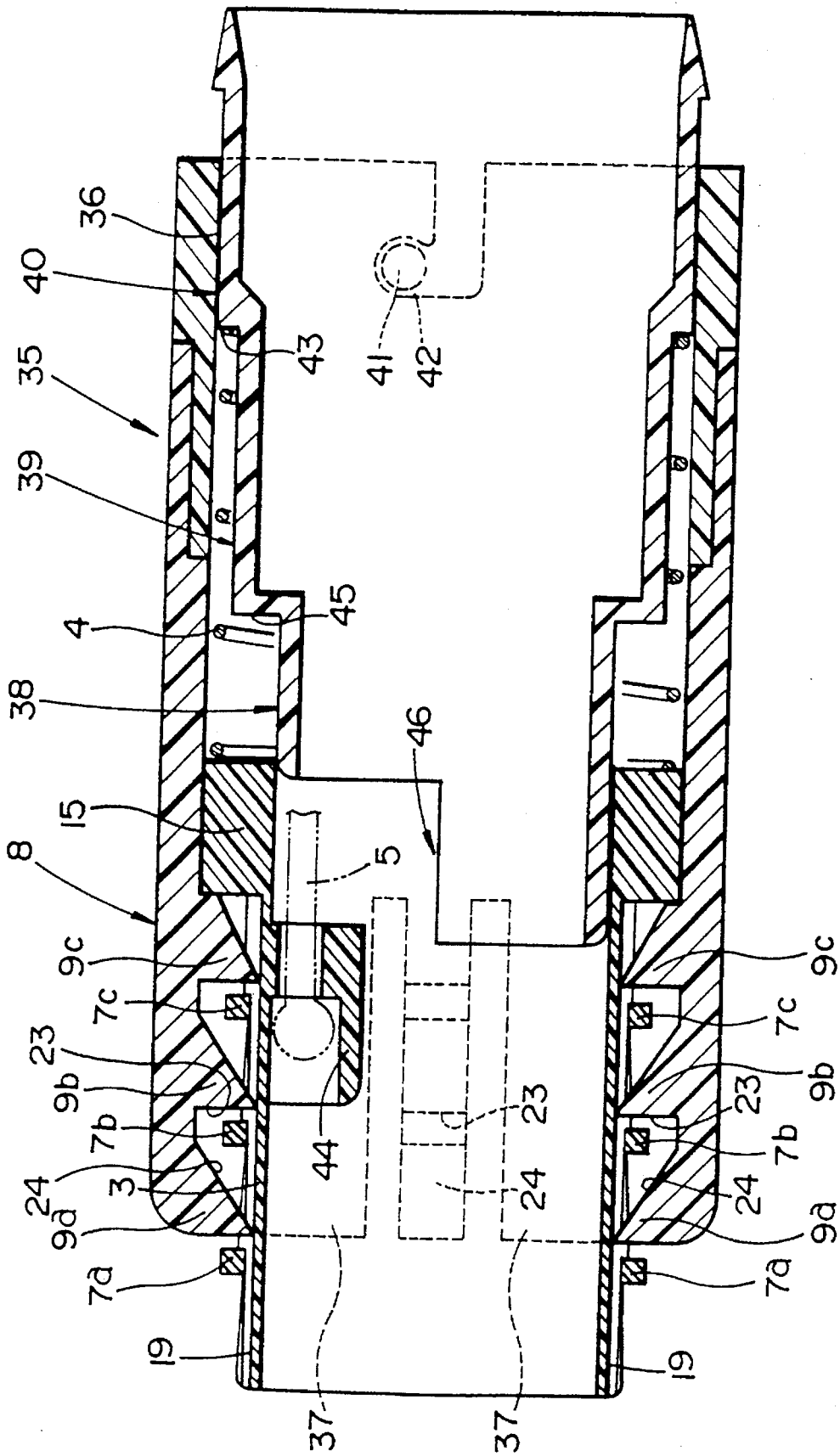

ENDOSCOPIC INSTRUMENT FOR LIGATING VARIX

BACKGROUND OF THE INVENTION

1. Field of the Invention

The present invention relates to a ligating instrument for use on the tip end of an endoscope for ligating a plurality of varices such as enlarged and tortuous veins that occur in an esophagus or any of other cavities in the body of a patient.

2. Description of the Prior Art

One known endoscopic ligating instrument is disclosed in U.S. Pat. No. 4,735,194. The disclosed endoscopic ligating instrument has an outer tube mounted on the tip end of an endoscope and an inner tube axially movably inserted in the outer tube. A trip wire has an end coupled to the inner tube, extends through a biopsy channel, and has an opposite end projecting out of the endoscope and joined to a handle. When the handle is pulled, the trip wire is axially moved to move the inner tube rearwardly into the outer tube. A ligating O-ring made of an elastomeric material is expanded radially outwardly and mounted on a tip end of the inner tube which projects out of the front end of the outer tube.

The endoscopic ligating instrument is used as follows: The endoscope is inserted into the esophagus, for example, of a patient until the tip end of the inner tube covers a varix to be ligated. Then, after a region where the varix exists is drawn into the inner tube under suction or the like, the handle is pulled to move the inner tube rearwardly into the outer tube. The ligating O-ring is now pushed off the inner tube by the tip end of the outer tube, and contracted radially inwardly, thereby ligating the base of the target lesion. Since the blood flow to the ligated varix is blocked, the ligated varix hardened and removed. The removal of the ligated varix finishes the treatment of the patient.

However, since only one ligating O-ring is mounted on the inner tube, if a plurality of varices are to be ligated successively, then it is necessary, each time a varix has been removed, to take the endoscope out of the cavity, replace the inner tube with a new inner tube with a ligating O-ring mounted thereon, and then insert the endoscope back into the cavity for ligating treatment. For ligating a plurality of varices, therefore, the endoscope is required to be inserted into and taken out of the cavity as many times as the number of varices to be ligated. Such a ligating practice has caused considerable pain to the patient.

SUMMARY OF THE INVENTION

It is therefore an object of the present invention to provide an endoscopic instrument for ligating a plurality of varices while it is being placed in a cavity, thereby reducing pains inflicted on the patient.

According to a first aspect of the present invention, there is provided an endoscopic instrument for ligating a plurality of varices, comprising an outer tube having a rear end for supporting a tip end of an endoscope, an inner tube axially movably mounted in the outer tube, a spring disposed in the outer tube for biasing the inner tube forwardly away from the rear end of the outer tube when the inner tube is moved rearwardly toward the rear end of the outer tube, a trip wire having an end coupled to the inner tube, extending through the endoscope supported by the rear end of the outer tube, and having an opposite end projecting out of the endo-scope, for moving the inner tube rearwardly against the bias of the spring when the opposite end of the trip wire is pulled, a plurality of resilient ring-shaped members resiliently expanded radially outwardly and mounted respectively at axially spaced positions on an outer circumferential surface of a portion of the inner tube which projects forwardly from a front end of the outer tube, a plurality of arms extending forwardly from the outer tube and disposed respectively at circumferentially equally spaced positions over the outer circumferential surface of the inner tube, and a plurality of axially spaced teeth mounted on each of the arms behind the resilient ring-shaped members respectively, the teeth having respective of pushing surfaces for abutting against and pushing the resilient ring-shaped members which are positioned respectively in front the teeth when the inner tube is moved rearwardly and respective rear slant surfaces for abutting against and riding over the resilient ring-shaped members which are positioned respectively behind the teeth, thereby spreading the arms radially outwardly, when the inner tube is moved forwardly, the arrangement being such that one, at a time, of the resilient ring-shaped members can be pushed forwardly off the inner tube by the front pushing surfaces of the teeth which are positioned foremost when the inner tube is moved rearwardly.

To ligate a plurality of varices in a cavity with the endoscopic instrument according to the first aspect of the present invention, the tip end of the endoscope is mounted in the rear end of the outer tube, and the endoscope is inserted into the cavity until the front end of the inner tube is held against a varix to be ligated. The varix is drawn into the inner tube by a suction device and kept in the drawn position. The trip wire is pulled to move the inner tube rearwardly against the resiliency of the spring. The resilient ring-shaped members mounted on the inner tube are pushed forwardly by the pushing surfaces of the teeth which are positioned behind the resilient ring-shaped members until the resilient ring-shaped member pushed by the pushing surfaces of the foremost teeth is forced off the inner tube. The base of the varix is now ligated by the resilient ring-shaped member pushed off the inner tube. The first ligating cycle is now finished.

Then, the trip wire is loosened, allowing the inner tube to move forwardly under the bias of the spring. The resilient ring-shaped members positioned behind the respective teeth abut against the slant surfaces of the teeth. At this time, the slant surfaces of the teeth are subjected to biasing forces from the spring through the resilient ring-shaped members. The biasing forces from the spring act to push the slant surfaces radially outwardly, spreading the arms radially outwardly. The teeth now ride over the resilient ring-shaped members. Continued forward movement of the inner tube causes the teeth to move past the resilient ring-shaped members and radially inwardly back to their original radial position.

The above process is repeated to ligate as many varices as the number of remaining resilient ring-shaped members on the inner tube. When the varices are ligated, the ligating treatment is finished.

Since the plural varices can be ligated while the endoscope remains inserted in the cavity, the endoscopic instrument can greatly reduce the pain which has heretofore been inflicted upon the patient during the ligating treatment.

Preferably, the outer tube has a plurality of separate tongues positioned circumferentially between the arms and extending along the arms, each of the arms being positioned between adjacent two of the separate tongues, the arms and the separate tongues having respective radially outer surfaces which jointly provide a substantially cylindrical surface.

Since the arms projecting over the outer circumferential surface of the inner tube are disposed between the separate tongues, there are no large gaps or recesses in the outer circumferential surface of the tip end of the endoscopic instrument. Accordingly, the endoscopic instrument can smoothly be inserted into the cavity.

The endoscopic instrument preferably further comprises a guide member disposed in the outer tube for guiding axial movement of the inner tube.

Even if the inner tube suffers off-center tension when the trip wire is pulled, the guide member guides the inner tube to move axially. The inner tube is thus prevented from being tilted, allowing the endoscopic instrument to ligate varices exactly and stably.

Preferably, the inner tube has a plurality of check surfaces behind the resilient ring-shaped members, respectively, for preventing the resilient ring-shaped members from being moved rearwardly when the rear slant surfaces abut against the resilient ring-shaped members in response to forward movement of the inner tube.

Because the check surfaces hold the resilient ring-shaped members securely on the inner tube, the teeth can ride reliably over the resilient ring-shaped members. Therefore, the endoscopic instrument operates highly reliably.

Preferably, the outer tube has a retainer for engaging and preventing the inner tube from dropping off the outer tube when the inner tube is moved most forwardly.

The retainer is effective to prevent the inner tube from being detached accidentally off the outer tube.

According to a second aspect of the present invention, there is also provided an endoscopic instrument for ligating a plurality of varices, comprising an outer tube having a rear end for supporting a tip end of an endoscope, an inner tube axially movably mounted in the outer tube, a trip wire having an end coupled to the inner tube, extending through the endoscope supported by the rear end of the outer tube, and having an opposite end projecting out of the endoscope, for moving the inner tube rearwardly when the opposite end of the trip wire is pulled, a plurality of resilient ring-shaped members resiliently expanded radially outwardly and mounted respectively at axially spaced positions on an outer circumferential surface of a portion of the inner tube which projects forwardly from a front end of the outer tube, the arrangement being such that the resilient ring-shaped members can be pushed forwardly by abutment against the outer tube and forced, one at a time, off the inner tube when the inner tube is moved rearwardly.

The endoscopic instrument according to the second aspect of the present invention is used to ligate a plurality of varices in a cavity as follows: The tip end of the endoscope is mounted in the rear end of the outer tube, and the endoscope is inserted into the cavity until the front end of the inner tube is held against a varix to be ligated. The varix is drawn into the inner tube by a suction device and kept in the drawn position. When the trip wire is pulled to move the inner tube rearwardly, the rearmost one of the resilient ring-shaped members mounted on the inner tube is held against and pushed forwardly by the outer tube. The pushed resilient ring-shaped member pushes the other resilient ring-shaped members positioned forwardly thereof until the foremost resilient ring-shaped member is forced off the inner tube. The base of the varix is now ligated by the resilient ring-shaped member pushed off the inner tube. The first ligating cycle is now finished.

The above process is repeated to ligate as many varices as the number of remaining resilient ring-shaped members on the inner tube. When the varices are ligated, the ligating treatment is finished.

Since the plural varices can be ligated while the endoscope remains inserted in the cavity, the endoscopic instrument according to the second aspect of the present invention can also greatly reduce the pain which has heretofore been inflicted upon the patient during the ligating treatment.

In the first and second aspects of the present invention, each of the resilient ring-shaped members preferably comprise an O-ring of rubber.

Since the resilient ring-shaped members made of rubber are highly durable against temperature changes caused when the endoscopic instrument is sterilized with heat, the resilient ring-shaped members can maintain their resiliency for a long period of time and are prevented from being deteriorated.

The above and other objects, features, and advantages of the present invention will become apparent from the following description when taken in conjunction with the accompanying drawings which illustrate preferred embodiments of the present invention by way of example.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 6 is an enlarged longitudinal cross-sectional view of a modification of the endoscopic ligating instrument according to the first embodiment of the present invention;

DETAILED DESCRIPTION OF THE PREFERRED EMBODIMENTS

Figure 1:
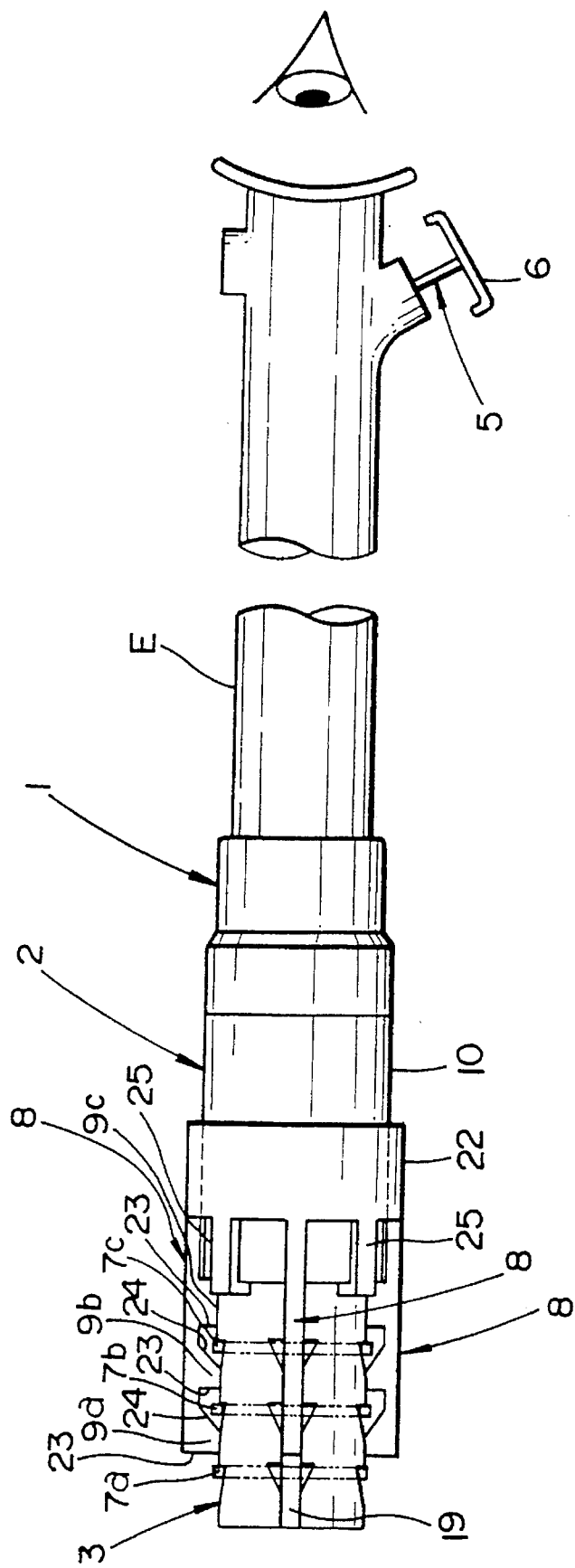
FIG. 1 is a fragmentary elevational view of an endoscope which incorporating an endoscopic ligating instrument according to a first embodiment of the present invention.
Figure 2:
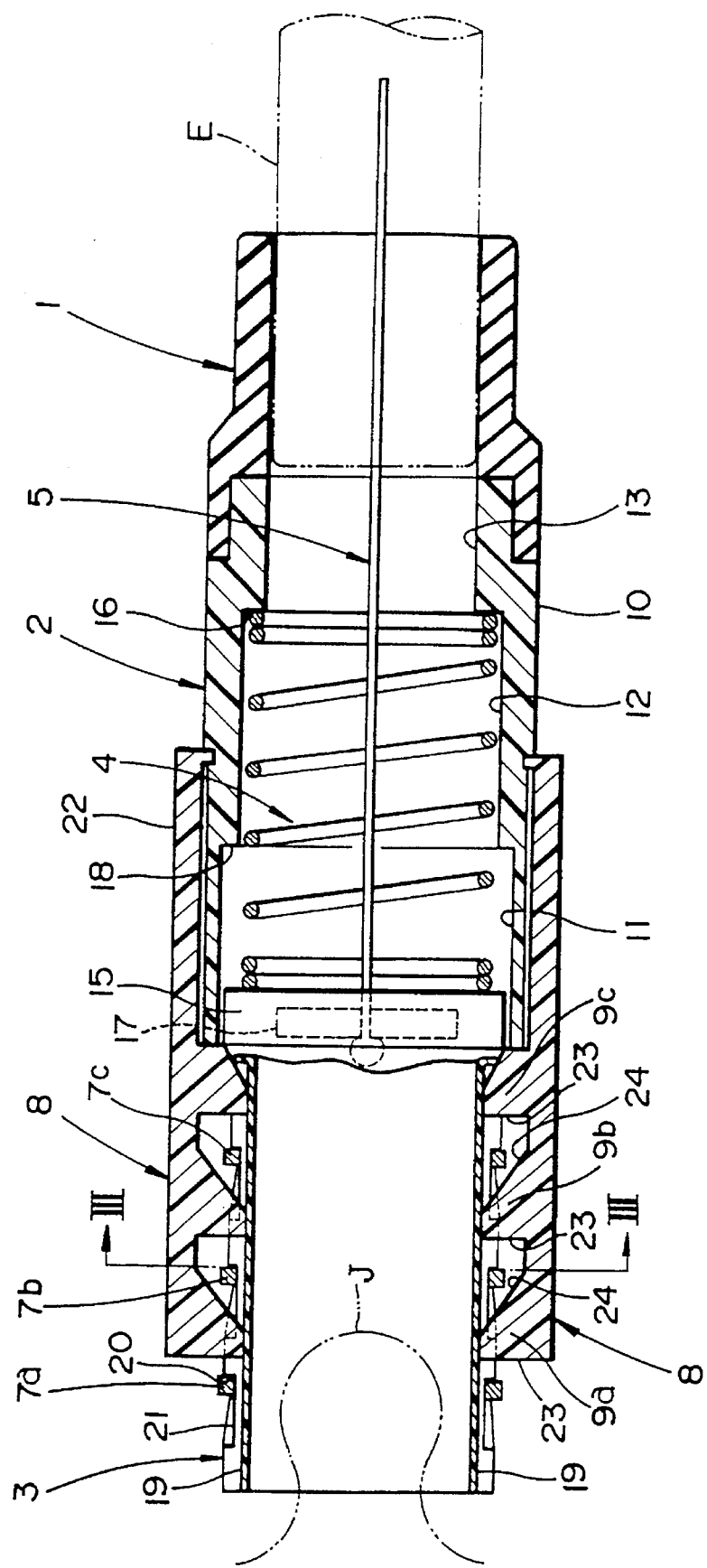
FIG. 2 is an enlarged longitudinal cross-sectional view of the endoscopic ligating instrument.
Figure 3:
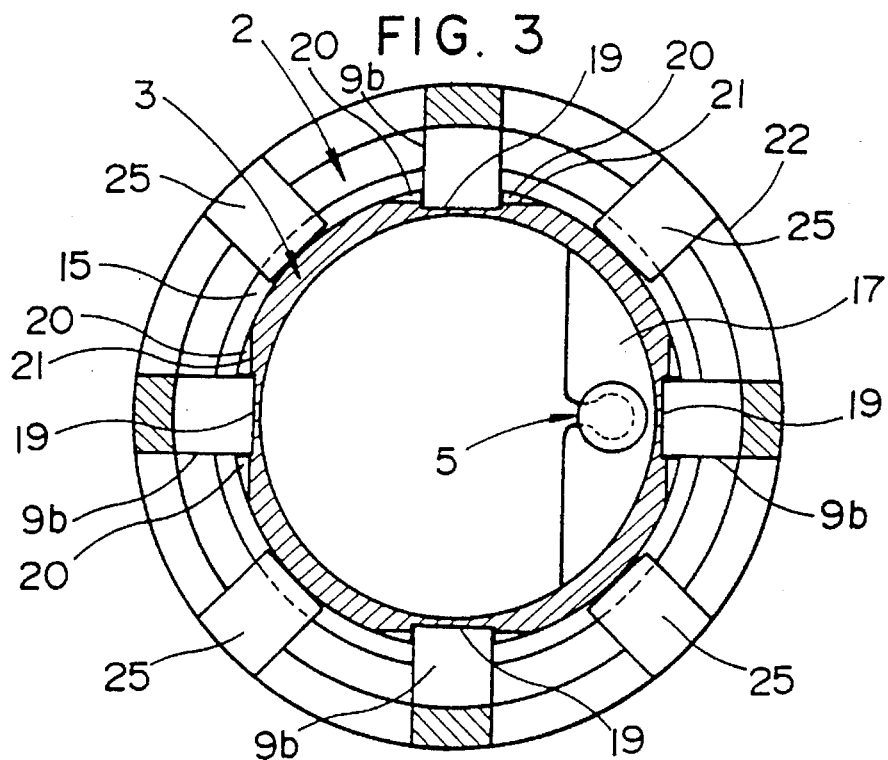
FIG. 3 is a cross-sectional view taken along line III—III of FIG. 2.
Figure 4:
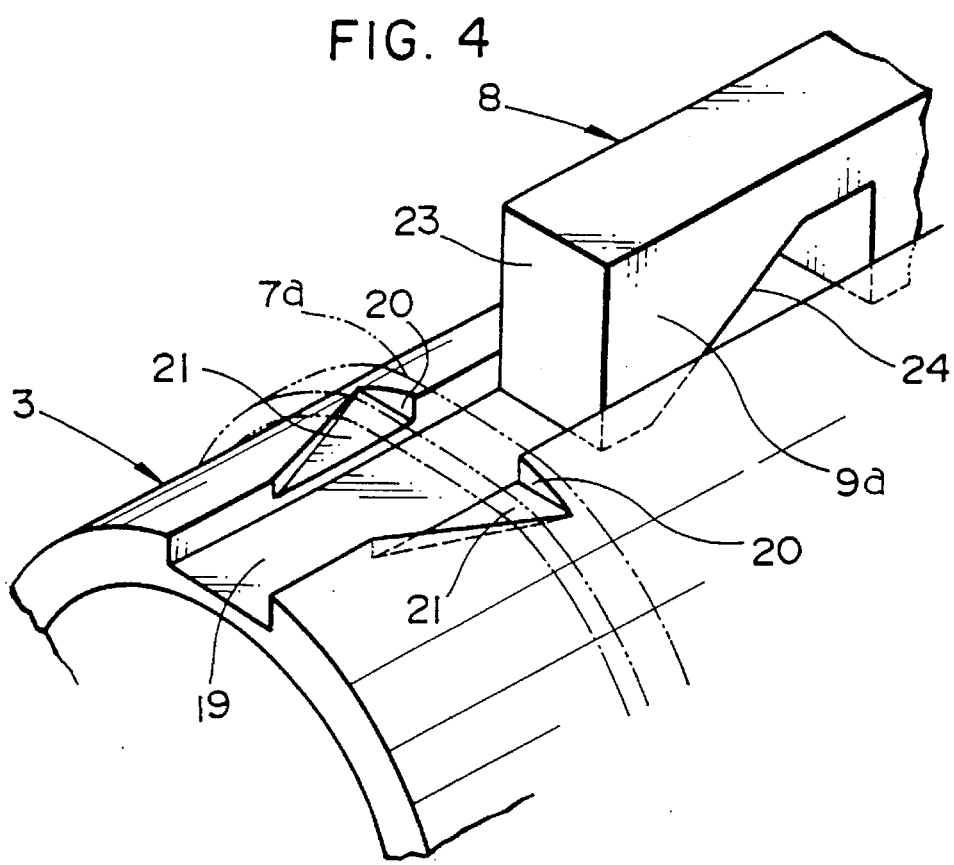
FIG. 4 is a fragmentary perspective view of a tip end portion of the endoscopic ligating instrument.

As shown in FIGS. 1 through 3, an endoscopic ligating instrument according to a first embodiment of the present invention includes an outer tube 2 having on its rear end an endoscope support 1 in which a tip end of an endoscope E is mounted, and an inner tube 3 axially movably inserted in the outer tube 2, the inner tube 3 projecting forwardly from a front end of the outer tube 2. A coil spring 4 is disposed in the outer tube 2 for normally biasing the inner tube 3 forwardly when the inner tube 3 has been moved rearwardly into the outer tube 2. A trip wire 5 has an end coupled to the inner tube 3, extends through a biopsy channel in the endoscope E, and has an opposite end projecting out of the endoscope E and joined to a handle 6. When the handle 6 is pulled, the trip wire 5 is axially moved to move the inner tube 3 rearwardly into the outer tube 2 against the bias of the coil spring 4. Three ligating O-rings 7a, 7b, 7c made of an elastomeric material are resiliently expanded radially outwardly and mounted respectively at axially equally spaced positions on the outer circumferential surface of a portion of the inner tube 3 which projects out of the front end of the outer tube 2. Four axial arms 8 extending forwardly from the outer tube 2 are disposed respectively at circumferentially equally spaced positions on the outer circumferential surface of the inner tube 3. Each of the arms 8 has axially spaced teeth 9a, 9b, 9c projecting radially inwardly and positioned axially behind the respective ligating O-rings 7a, 7b, 7c for individual abutment against the ligating O-rings 7a, 7b, 7c upon axial movement of the inner tube 3.

Specific details of the various parts of the endoscopic ligating instrument will be described below.

The outer tube 2 has a cylindrical body 10 made of a relatively hard, transparent synthetic resin such as ABS resin, polycarbonate resin, styrene resin, polyvinyl chloride resin, or the like. As shown in FIG. 2, the cylindrical body 10 has a larger-diameter hole 11, a medium-diameter hole 12, and a smaller-diameter hole 13 which are defined therein successively from its front end toward its rear end. The endoscope support 1 is in the form of a cylindrical body made of a soft polyvinyl chloride resin or any of various rubbers, and has a front end fitted over the rear end of the cylindrical body 10. The tip end of the endoscope E is mounted in the rear end of the endoscope support 1.

The inner tube 3 is in the form of a cylindrical body made of a relatively hard, transparent synthetic resin such as ABS resin, polycarbonate resin, styrene resin, polyvinyl chloride resin, or the like. The inner tube 3 projects forwardly from the front end of the outer tube 2, and is axially movably inserted in the larger-diameter hole 11 in the outer tube 2. The inner tube 3 has a short larger-diameter portion 15 on its rear end. The coil spring 4 in the outer tube 2 extends axially between the short larger-diameter portion 15 and a radial step 16 between the medium-diameter hole 12 and the smaller-diameter hole 13 of the outer tube 2, and has opposite ends held against the short larger-diameter portion 15 and the radial step 16, respectively.

As shown in FIGS. 2 and 3, the short larger-diameter portion 15 has a wire joint 17 on its inner circumferential surface. The trip wire 5, which comprises a metallic wire made of stainless steel or a braided cord of metallic strands made of stainless steel or a synthetic resin wire made of a synthetic resin having high tensile strength, such as nylon, is connected at one end thereof to the wire joint 17. The trip wire 5 extends through the biopsy channel in the endoscope E and has its other end projecting out of the endoscope E and connected to the handle 6 as shown in FIG. 1. When the trip wire 5 is pulled rearwardly by the handle 6, the inner tube 3 is moved rearwardly in the larger-diameter hole 11 against the bias of the coil spring 4. The inner tube 3 can be moved rearwardly in the larger-diameter hole 11 until the larger-diameter portion 15 abuts against a radial step 18 between the larger-diameter hole 11 and the medium-diameter hole 12 in the outer tube 2, whereupon the inner tube 3 is prevented from being moved further rearwardly. When the trip wire 5 is loosened, the inner tube 3 is moved forwardly to the position shown in FIG. 1 under the bias of the coil spring 4.

The outer circumferential surface of the portion of the inner tube 3 which projects from the outer tube 2 has four axial slide grooves 19 defined therein for the teeth 9a, 9b, 9c of the arms 8 to be axially slidably moved therein when the inner tube 3 is axially moved. The slide grooves 19 are located respectively at circumferentially equally spaced positions on the inner tube 3 in radial alignment with the respective arms 8, as shown in FIG. 3. The three ligating O-rings 7a, 7b, 7c are resiliently expanded radially outwardly and mounted on the outer circumferential surface of the portion of the inner tube 3 which projects from the outer tube 2 at respective axially equal positions. The ligating O-rings 7a, 7b, 7c are made of natural rubber or natural rubber containing a reinforcing material such as carbon or synthetic rubber. Since the ligating O-rings 7a, 7b, 7c made of rubber are highly durable against temperature changes caused when the endoscopic ligating instrument is sterilized with heat, the ligating O-rings 7a, 7b, 7c can maintain their resiliency for a long period of time and is prevented from being deteriorated.

As shown in FIGS. 1 and 2, the arms 8 extend forwardly from a cylindrical member 22 detachably fitted over a front end portion of the outer tube 2 and are positioned over the outer circumferential surface of the inner tube 3 in radial alignment with the respective slide grooves 19. The arms 8 and the cylindrical member 22 are integrally formed of a relatively hard, transparent synthetic resin such as ABS resin, polycarbonate resin, styrene resin, polyvinyl chloride resin, or the like. The teeth 9a, 9b, 9c which can slide in the slide grooves 19 when the inner tube 3 is axially moved are mounted on radially inner surfaces of the arms 8 which confront the respective slide grooves 19 at axially spaced positions behind the respective ligating O-rings 7a, 7b, 7c.

Figure 5A:
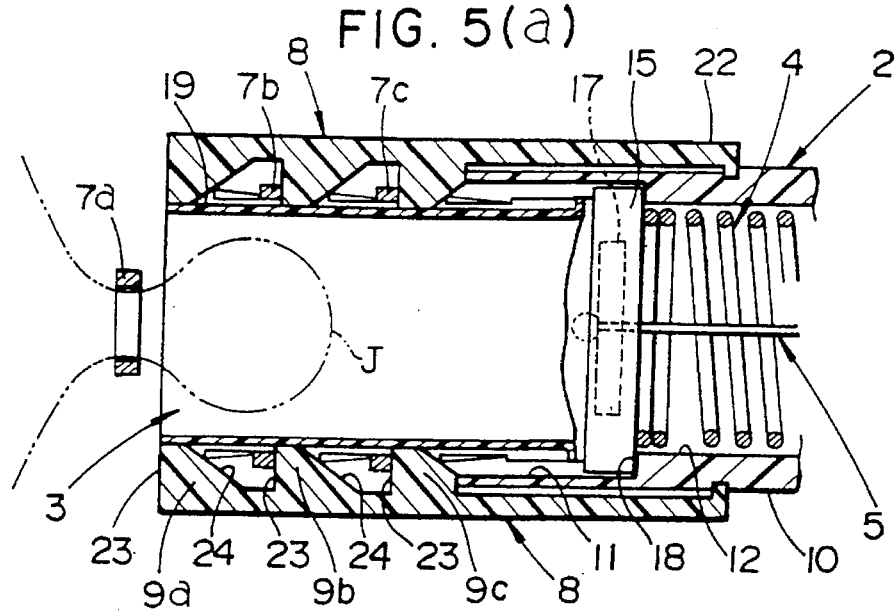
FIG. 5 (a) is a fragmentary longitudinal cross-sectional view of the endoscopic ligating instrument which is used in a ligating process.
FIG. 5(b) is a fragmentary longitudinal cross-sectional view showing the manner in which the endoscopic ligating instrument operates to ligate a varix.
FIG. 5(c) is a fragmentary longitudinal cross-sectional view showing the parts of the endoscopic ligating instrument which are positioned when one ligating cycle is completed.
Figure 5B:
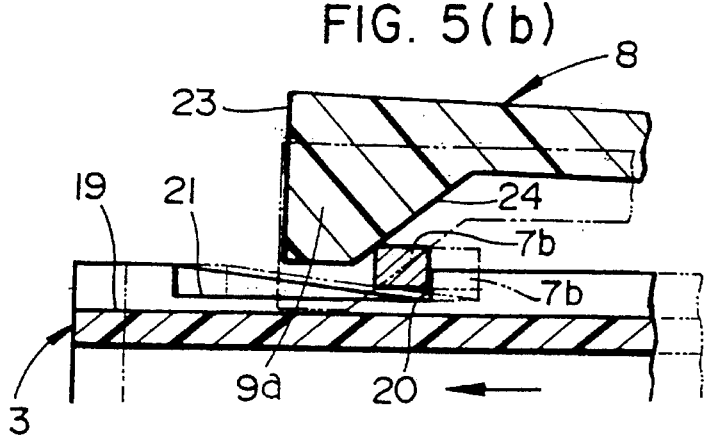

The teeth 9a, 9b, 9c have respective radial front pushing surfaces 23 which can engage and push forwardly ligating O-rings when the inner tube 3 is moved rearwardly into the outer tube 2. When the inner tube 3 is moved rearwardly into the outer tube 2 until the larger-diameter portion 15 abuts against the step 18 as shown in FIG. 5(a), the ligating O-ring 7a is pushed off the inner tube 3 by the front pushing surfaces 23 of the foremost teeth 9a, and the ligating O-rings 7b, 7c are pushed by the front pushing surfaces 23 of the other teeth 9b, 9c into the respective positions which were occupied by the ligating O-rings 7a, 7b, respectively. The teeth 9a, 9b, 9c also have respective rear slant surfaces 24 which can ride over rear ligating O-rings while spreading the arms 8 radially outwardly when the inner tube 3 is moved forwardly, as shown in FIG. 5(b).

The outer circumferential surface of the inner tube 3 also has four circumferentially equally spaced radial check shoulders 20 disposed immediately behind the position in which the ligating O-ring 7a is mounted, and four circumferentially equally spaced radial check shoulders 20 disposed immediately behind the position in which the ligating O-ring 7b is mounted. These radial check shoulders 20 serve to prevent ligating O-rings from being moved rearwardly when the slant surfaces of the teeth 9a, 9b engage the ligating O-rings. Each of the radial check shoulders 20 is formed by producing substantially triangular flat surfaces 21, each spreading rearwardly from a side wall of one of the slide grooves 19, one on each side of one of the slide grooves 19, and then producing radial surfaces extending perpendicularly to rear edges of these flat surfaces 21.

Four axial retainers 25 are integrally formed with and extend forwardly from the cylindrical member 22. The retainers 25 are positioned circumferentially between the arms 8 for engagement with the front surface of the larger-diameter portion 15 to prevent the inner tube 3 from dropping off the outer tube 2 when the inner tube 3 is moved most forwardly.

The endoscopic ligating instrument is used to ligate a plurality of varices in a cavity in the body of a patient as follows: The tip end of the endoscope E is mounted in the endoscope support 1, and then the endoscope E is inserted into the cavity. After the front end of the inner tube 3 has been held against a varix J to be ligated, the varix J is drawn into the inner tube 3 by a suction device (not shown) and kept in the drawn position. Now, the base of the varix J is positioned at the front end of the inner tube 3. Then, the handle 6 is pulled to draw the trip wire 5 for thereby retracting the inner tube 3 rearwardly against the resiliency of the coil spring 4. As shown in FIG. 5(a), the ligating O-rings 7a, 7b, 7c mounted on the inner tube 3 are pushed forwardly by the pushing surfaces 23 of the teeth 9a, 9b, 9c, respectively, which slide in the slide grooves 19 behind the ligating O-rings 7a, 7b, 7c until the ligating O-ring 7a pushed by the pushing surfaces 23 of the foremost teeth 9a is forced off the inner tube 3 and the ligating O-rings 7b, 7c pushed by the pushing surfaces 23 of the foremost teeth 9b, 9c are moved to the positions initially occupied by the respective ligating O-rings 7a, 7b. The base of the varix J is now ligated by the ligating O-ring 7a pushed off the inner tube 3. The first ligating cycle is now finished.

Figure 5C:
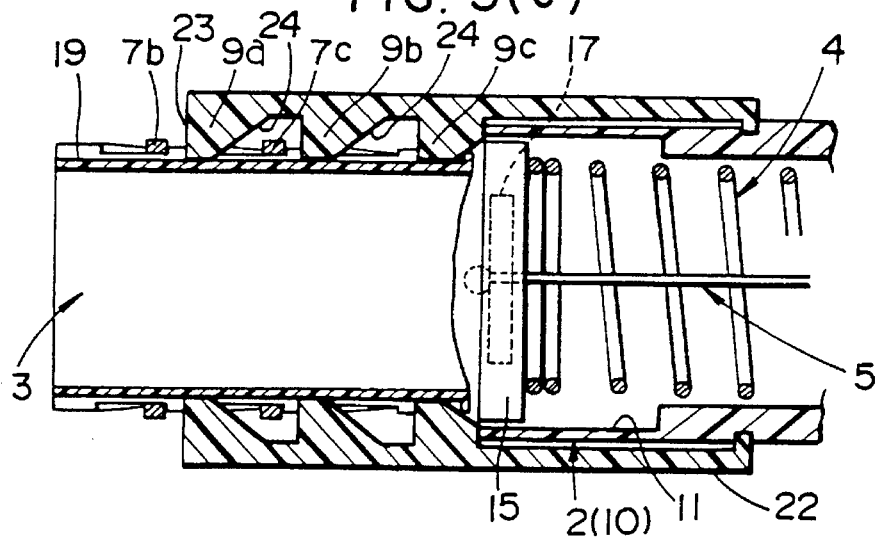

Then, the trip wire 5 is loosened, allowing the inner tube 3 to move forwardly under the bias of the coil spring 4. The teeth 9a, 9b, 9c slide relatively rearwardly in the slide grooves 19, and the ligating O-rings 7b, 7c positioned behind the respective teeth 9a, 9b abut against the slant surfaces 24 of the teeth 9a, 9b. At this time, the slant surfaces 24 of the teeth 9a, 9b are subjected to biasing forces from the coil spring 4 through the ligating O-rings 7b, 7c. As shown in FIG. 5(b), the biasing forces from the coil spring 4 act to push the slant surfaces 24 radially outwardly, spreading the arms 8 radially outwardly. The teeth 9a, 9b now ride over the ligating O-rings 7b, 7c. Continued forward movement of the inner tube 3 causes the teeth 9a, 9b to move past the ligating O-rings 7b, 7c and radially inwardly back to their original radial position, as shown in FIG. 5(c). When the teeth 9a, 9b are moved back radially inwardly, the ligating O-rings 7b, 7c are positioned in front of the teeth 9a, 9b, respectively. At the time the slant surfaces 24 of the teeth 9a, 9b abut against the ligating O-rings 7b, 7c, as shown in FIG. 5(b), the ligating O-rings 7b, 7c are pushed rearwardly by the slant surfaces 24, but are prevented from moving rearwardly by the check shoulders 20. Consequently, the teeth 9a, 9b can reliably ride over the ligating O-rings 7b, 7c which are securely held in position.

The endoscope E is then moved to another varix J in the cavity, and the above process is repeated to ligate the varix J with the ligating O-ring 7b. Still another varix J in the cavity can also be ligated by the ligating O-ring 7c by repeating the above process. When these varices J are ligated, the ligating treatment is finished.

A modification of the endoscopic ligating instrument according to the first embodiment will be described below with reference to FIGS. 6 and 7. Those parts shown in FIGS. 6 and 7 which are identical to those shown in FIGS. 1 through 5(a)–5(c) are denoted by identical reference numerals, and will not be described in detail below.

Figure 7:
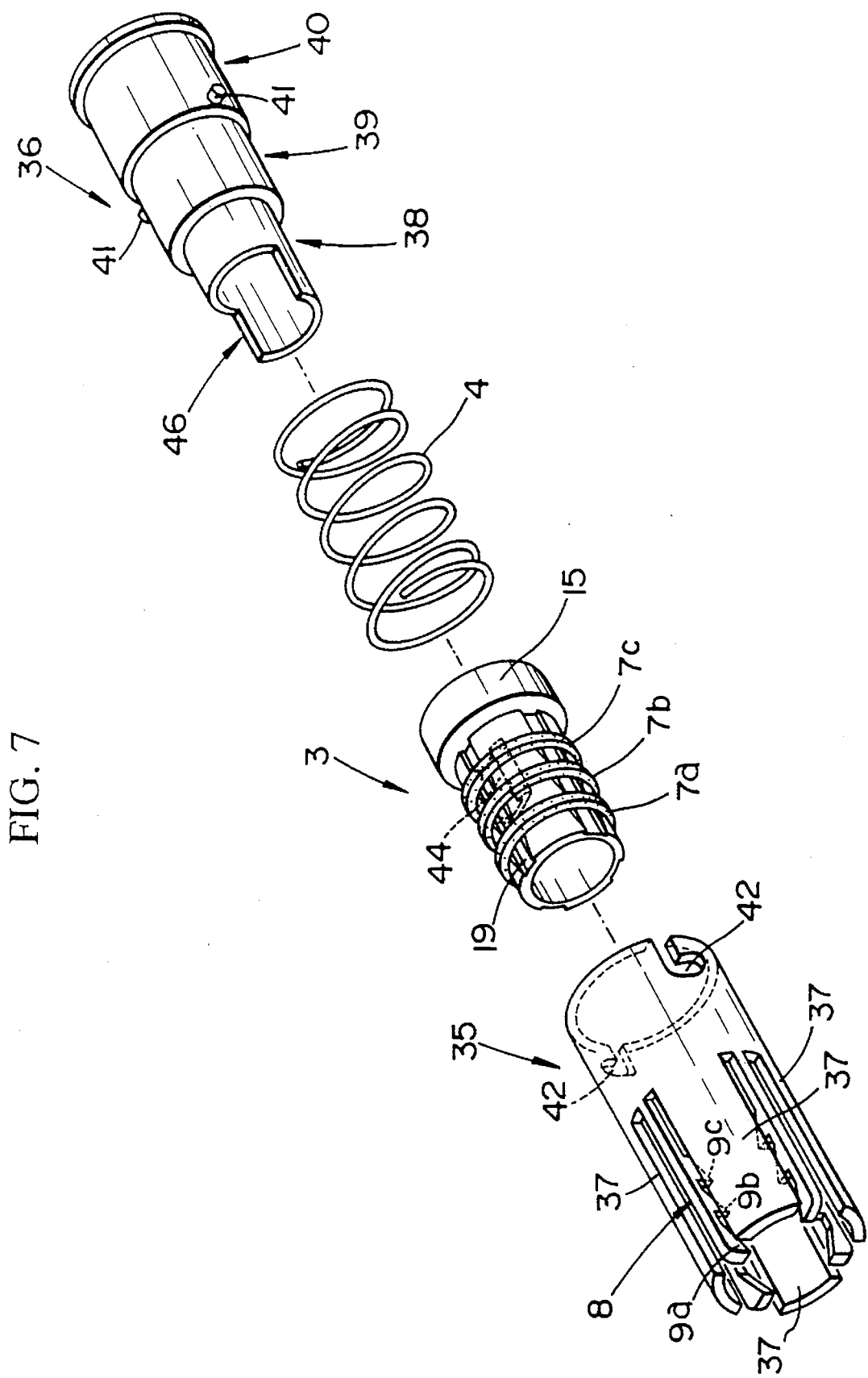
FIG. 7 is an exploded perspective view of the modified endoscopic ligating instrument shown in FIG. 6.

As shown in FIGS. 6 and 7, the modified endoscopic ligating instrument comprises an outer tube 35, a guide member 36 fixedly mounted in a rear end portion of the outer tube 35, and an inner tube 3 axially movably inserted in the outer tube 35 and projecting forwardly from a front end of the outer tube 35. The outer tube 35 houses therein a coil spring 4 for biasing the inner tube 3 forwardly when the inner tube 3 is moved rearwardly. A trip wire 5 has an end coupled to the inner tube 3, extends through a biopsy channel in an endoscope which may be identical to the endoscope E shown in FIG. 1, and has an opposite end projecting out of the endoscope. When the trip wire 5 is pulled, the inner tube 3 is moved rearwardly into the outer tube 35 against the bias of the coil spring 4. Three ligating O-rings 7a, 7b, 7c are resiliently expanded radially outwardly and mounted respectively at axially equally spaced positions on the outer circumferential surface of a portion of the inner tube 3 which projects out of the front end of the outer tube 35. Four axial arms 8 extending forwardly from the outer tube 35 are disposed respectively at circumferentially equally spaced positions on the outer circumferential surface of the inner tube 3. Each of the arms 8 has axially spaced teeth 9a, 9b, 9c projecting radially inwardly and positioned axially behind the respective ligating O-rings 7a, 7b, 7c for individual abutment against the ligating O-rings 7a, 7b, 7c upon axial movement of the inner tube 3. As shown in FIG. 7, four separate tongues 37 extend forwardly from the outer tube 35 and are located in circumferentially equally spaced positions between the arms 8.

The various parts of the endoscopic ligating instrument will be described below in specific detail.

The outer tube 35 is of a cylindrical shape and made of a relatively hard, transparent synthetic resin such as ABS resin, polycarbonate resin, styrene resin, polyvinyl chloride resin, or the like. The guide member 36, which is tubular in shape, is fixedly disposed in the outer tube 35 and has a rear end portion exposed out of the outer tube 35. As shown in FIG. 6, the guide member 36 comprises a smaller-diameter portion 38, a medium-diameter portion 39, and a larger-diameter portion 40 which are arranged successively from the front end to the rear end of the guide member 36. The smaller-diameter portion 38, the medium-diameter portion 39, and the larger-diameter portion 40 have smaller, medium, and larger outside diameters, respectively. As shown in FIG. 7, the guide member 36 has a pin 41 projecting radially outwardly from the rear end thereof. The pin 41 engages in a groove 42 defined in the rear end of the outer tube 35, thereby joining the guide member 36 the outer tube 35 with each other. The tip end of the endoscope is mounted in the rear end of the guide member 36. As shown in FIG. 7, each of the arms 8 is positioned between adjacent two of the separate tongues 37. The arms 8 and the separate tongues 37 have respective radially outer surfaces which jointly provide a substantially cylindrical surface that is free of large gaps or recesses and hence allows the endoscopic ligating instrument to be inserted smoothly into a cavity. The separate tongues 37 serve to protect the outer circumferential surface of the front end portion of the inner tube 3.

As illustrated in FIGS. 6 and 7, the inner tube 3 is of a cylindrical shape and made of a relatively hard, transparent synthetic resin Such as ABS resin, polycarbonate resin, styrene resin, polyvinyl chloride resin, or the like. The inner tube 3 as it projects from the front end of the outer tube 35 is axially movably inserted between an inner wall surface of the outer tube 35 and an outer wall surface of the smaller-diameter portion 38 of the guide member 36. The inner tube 3 has a short larger-diameter portion 15 on its rear end. The coil spring 4 in the outer tube 35 extends axially between the short larger-diameter portion 15 and a radial step 43 between the medium-diameter portion 39 and the larger-diameter portion 40 of the guide member 36, and has opposite ends held against the short larger-diameter portion 15 and the radial step 43, respectively.

As shown in FIG. 6, the inner tube 3 has a wire joint 44 on its inner circumferential surface near the short larger-diameter portion 15. One end of the trip wire 5 is detachably connected to the wire joint 44. When the other end of the trip wire 5 is pulled, the inner tube 3 is moved rearwardly in the outer tube 35 against the bias of the coil spring 4. The inner tube 3 can be moved rearwardly in the outer tube 35 until the larger-diameter portion 15 abuts against a radial step 45 between the smaller-diameter portion 38 and the medium-diameter portion 39 of the guide member 36, whereupon the inner tube 3 is prevented from being moved further rearwardly. When the trip wire 5 is loosened, the inner tube 3 is moved forwardly to the position shown in FIG. 6 under the bias of the coil spring 4. The smaller-diameter portion 38 of the guide member 36 has a recess 46 defined therein for keeping the smaller-diameter portion 38 clear of the wire joint 44 when the inner tube 3 is moved rearwardly. The smaller-diameter portion 38 of the guide member 36 serves as a guide for guiding the inner tube 3 to move linearly axially between itself and the outer tube 35 while preventing the inner tube 3 from being tilted when the inner tube 3 is subjected to off-center tension by the wire joint 44 that is pulled by the trip wire 5.

The slide grooves 19 in the inner tube 3 and the teeth 9a, 9b, 9c of the arms 8 are identical to those which are shown in FIGS. 1 through 5(a)–5(c).

Use of the modified endoscopic ligating instrument to ligate a plurality of varices in a cavity in the body of a patient will be described below. The endoscope combined with the modified endoscopic ligating instrument is inserted into the cavity. Since the arms 8 are positioned between the separate tongues 37, as shown in FIG. 7, the modified endoscopic ligating instrument can smoothly be inserted into the cavity. After the front end of the inner tube 3 has been held against a varix to be ligated, the varix is drawn into the inner tube 3 by a suction device (not shown) and kept in the drawn position. Now, the base of the varix J is positioned at the front end of the inner tube 3. Then, the trip wire 5 is pulled to retract the inner tube 3 rearwardly against the resiliency of the coil spring 4. At this time, because the rear end of the inner tube 3 is moved while being held between the smaller-diameter portion 38 of the guide member 36 and the outer tube 35, as shown in FIG. 6, the inner tube 3 is not tilted, and hence can be positioned reliably with respect to the varix without undesirable displacement for accurate ligating operation. The ligating O-ring 7a pushed by the pushing surfaces 23 of the foremost teeth 9a is forced off the inner tube 3, ligating the varix. The first ligating cycle is now finished.

Then, the trip wire 5 is loosened, allowing the inner tube 3 to move forwardly under the bias of the coil spring 4. As described above with reference to FIG. 5(b), the arms 8 are spread radially outwardly, and the teeth 9a, 9b ride over the ligating O-rings 7b, 7c and then are moved radially inwardly back, whereupon the ligating O-rings 7b, 7c are positioned in front of the teeth 9a, 9b, respectively.

The endoscope is then moved to other varices in the cavity, and the above process is repeated to ligate the varices with the ligating O-rings 7b, 7c. When these varices are ligated, the ligating treatment is finished.

An endoscopic ligating instrument according to a second embodiment of the present invention will be described below with reference to FIGS. 8 and 9.

Figure 8:
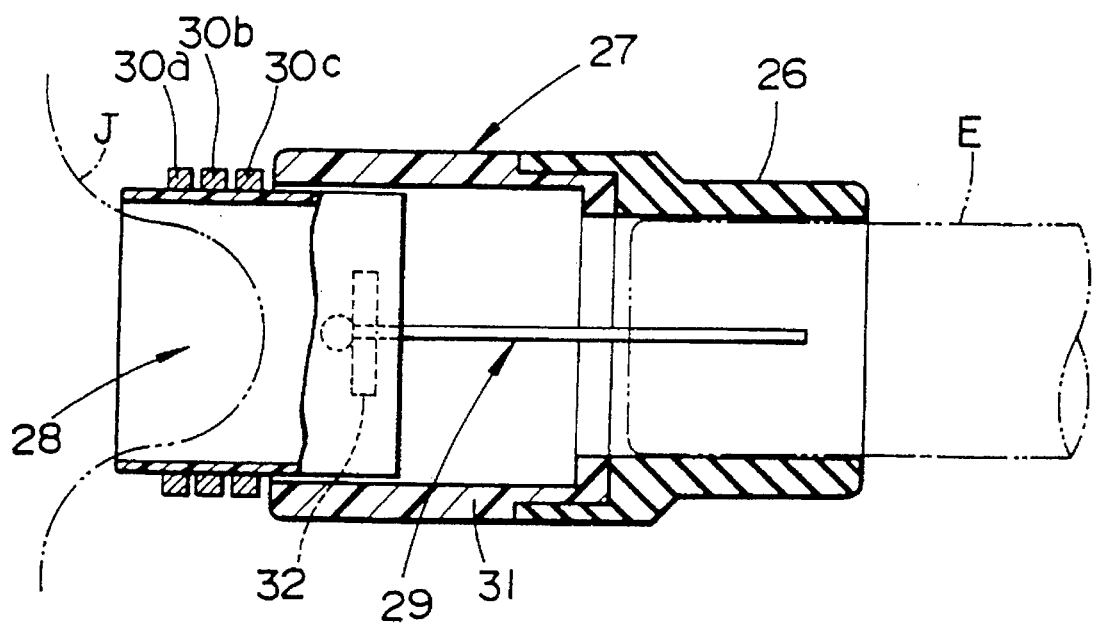
FIG. 8 is a longitudinal cross-sectional view of an endoscopic ligating instrument according to a second embodiment of the present invention.
Figure 9:
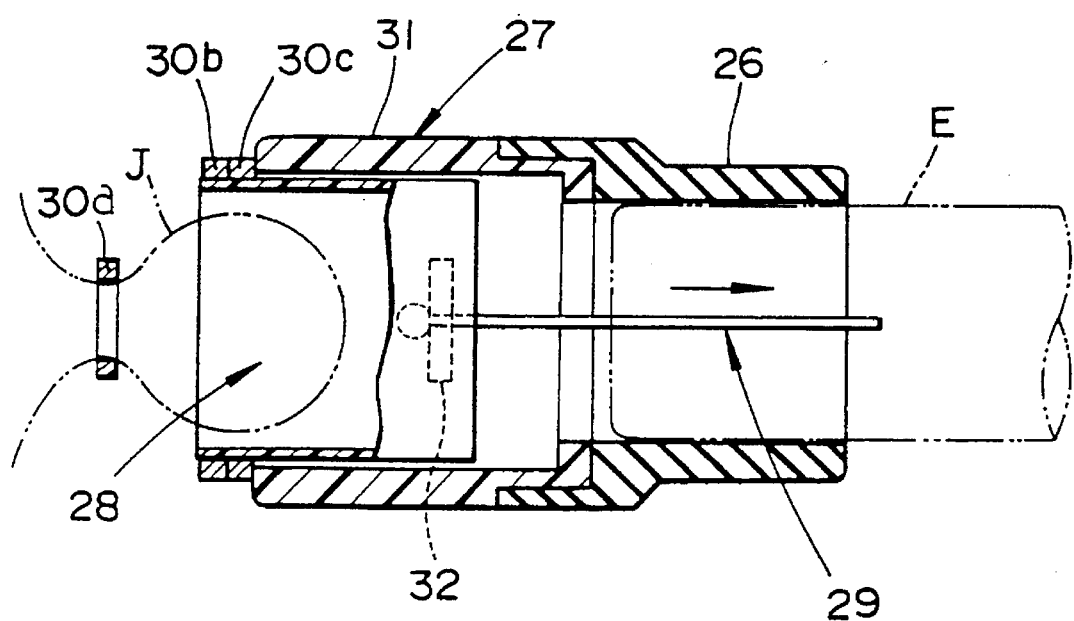
FIG. 9 is a longitudinal cross-sectional view showing the manner in which the endoscopic ligating instrument shown in FIG. 8 operates to ligate a varix.

As shown in FIGS. 8 and 9, the endoscopic ligating instrument comprises an outer tube 27 having on its rear end an endoscope support 26 in which a tip end of an endoscope E is mounted, and an inner tube 28 axially movably inserted in the outer tube 27. A trip wire 29 has an end coupled to the inner tube 28, extends through a biopsy channel in the endoscope E, and has an opposite end projecting out of the endoscope E and joined to a handle (not shown). Three ligating O-rings 30a, 30b, 30c made of an elastomeric material are resiliently expanded radially outwardly and mounted respectively at axially equally spaced positions on the outer circumferential surface of a portion of the inner tube 28 which projects out of the front end of the outer tube 27.

The outer tube 27 has a cylindrical body 31 made of a relatively hard, transparent synthetic resin such as ABS resin, polycarbonate resin, styrene resin, polyvinyl chloride resin, or the like. The endoscope support 26 is in the form of a cylindrical body made of a soft polyvinyl chloride resin or any of various rubbers, and has a front end fitted over the rear end of the cylindrical body 31. The tip end of the endoscope E is mounted in the rear end of the endoscope support 26.

The inner tube 28 is in the form of a cylindrical body made of a relatively hard, transparent synthetic resin such as ABS resin, polycarbonate resin, styrene resin, polyvinyl chloride resin, or the like. The inner tube 28 is axially movably inserted in the cylindrical body 31. the inner tube 28 has a wire joint 32 on its inner circumferential surface near the rear end thereof. The trip wire 29, which comprises a metallic wire made of stainless steel or a braided cord of metallic strands made of stainless steel or a synthetic resin wire made of a synthetic resin having high tensile strength, such as nylon, is connected at one end thereof to the wire joint 32. The trip wire 29 extends through the biopsy channel in the endoscope E and has its other end projecting out of the endoscope E and connected to the handle. When the trip wire 29 is pulled rearwardly by the handle, the inner tube 28 is moved rearwardly in the cylindrical body 31.

The ligating O-rings 30a, 30b, 30c are made of natural rubber or natural rubber containing a reinforcing material such as carbon or synthetic rubber. Since the ligating O-rings 30a, 30b, 30c made of rubber are highly durable against temperature changes caused when the endoscopic ligating instrument is sterilized with heat, the ligating O-rings 7a, 7b, 7c can maintain their resiliency for a long period of time and is prevented from being deteriorated. When the inner tube 28 is moved rearwardly, the ligating O-ring 30c abuts against the front end of the outer tube 27.

A plurality of varices in a cavity in the body of a patient can be ligated by the endoscopic ligating instrument as follows: The tip end of the endoscope E is mounted in the endoscope support 26, and then the endoscope E is inserted into the cavity. After the front end of the inner tube 28 has been held against a varix J to be ligated, the varix J is drawn into the inner tube 28 by a suction device (not shown) and kept in the drawn position, as shown in FIG. 8. Now, the base of the varix J is positioned at the front end of the inner tube 28. Then, the handle is pulled to draw the trip wire 29 for thereby retracting the inner tube 28 rearwardly. The rearmost ligating O-ring 30c on the inner tube 28 is now held against the front end of the outer tube 27, and pushed forwardly thereby. The ligating O-ring 30c then pushes forwardly the ligating O-rings 30a, 30b that are positioned on the inner tube 28 in front of the ligating O-ring 30c, until the foremost ligating O-ring 30a is forced off the inner tube 28, as shown in FIG. 9. The base of the varix J is now ligated by the ligating O-ring 30a pushed off the inner tube 28. The first ligating cycle is now finished.

Then, the endoscope E is then moved successively to other varices J in the cavity, and the above process is repeated to ligate the varices J with the ligating O-rings 7b, 7c. When these varices J are ligated, the ligating treatment is finished.

Although certain preferred embodiments of the present invention has been shown and described in detail, it should be understood that various changes and modifications may be made therein without departing from the scope of the appended claims.

What is claimed is:

1. An endoscopic instrument for ligating a plurality of varices, comprising:

an outer tube having a rear end for supporting a tip end of an endoscope;

an inner tube axially movably mounted in said outer tube;

a trip wire having an end coupled to said inner tube for extending through the endoscope supported by the rear end of the outer tube, and having an opposite end for projecting out of the endoscope, for moving said inner tube rearwardly when said opposite end of the trip wire is pulled;

a plurality of resilient ring-shaped members resiliently expanded radially outwardly and mounted respectively at axially spaced positions on an outer circumferential surface of a portion of said inner tube which projects forwardly from a front end of said outer tube, said ring-shaped members being expanded substantially equally and mounted on said inner tube at positions having substantially equal diameters, and means for forwardly pushing each of said resilient ring-shaped members, one at a time, off of said inner tube by abutment against said outer tube when said inner tube is moved rearwardly.

2. An endoscopic instrument according to claim 1, wherein each of said resilient ring-shaped members comprises an O-ring of rubber.

3. An endoscopic instrument for ligating a plurality of varices, comprising:

an outer tube having a rear end for supporting a tip end of an endoscope;

an inner tube axially movably mounted in said outer tube;

a spring disposed in said outer tube for biasing said inner tube forwardly away from said rear end of the outer tube when the inner tube is moved rearwardly toward said rear end of the outer tube;

a trip wire having an end coupled to said inner tube, for extending through the endoscope supported by the rear end of the outer tube, and having an opposite end for projecting out of the endoscope, for moving said inner tube rearwardly against the bias of said spring when said opposite end of the trip wire is pulled;

a plurality of resilient ring-shaped members resiliently expanded radially outwardly and mounted respectively at axially spaced positions on an outer circumferential surface of a portion of said inner tube which projects forwardly from a front end of said outer tube;

a plurality of arms extending forwardly from said outer tube and disposed respectively at circumferentially equally spaced positions over the outer circumferential surface of said inner tube; and a plurality of axially spaced teeth mounted on each of said arms behind said resilient ring-shaped members respectively, said teeth having respective front pushing surfaces for abutting against and pushing the resilient ring-shaped members which are positioned respectively in front the teeth when said inner tube is moved rearwardly and respective rear slant surfaces for abutting against and riding over the resilient ring-shaped members which are positioned respectively behind the teeth, thereby spreading said arms radially outwardly, when said inner tube is moved forwardly, the arrangement being such that one, at a time, of said resilient ring-shaped members can be pushed forwardly off said inner tube by the front pushing surfaces of the teeth which are positioned foremost when said inner tube is moved rearwardly.

4. An endoscopic instrument according to claim 3, wherein said outer tube has a plurality of separate tongues positioned circumferentially between said arms and extending along said arms, each of said arms being positioned between adjacent two of said separate tongues, said arms and said separate tongues having respective radially outer surfaces which jointly provide a substantially cylindrical surface.

5. An endoscopic instrument according to claim 4, further comprising a guide member disposed in said outer tube for guiding axial movement of said inner tube.

6. An endoscopic instrument according to claim 4, wherein said inner tube has a plurality of check surfaces behind said resilient ring-shaped members, respectively, for preventing the resilient ring-shaped members from being moved rearwardly when said rear slant surfaces abut against the resilient ring-shaped members in response to forward movement of said inner tube.

7. An endoscopic instrument according to claim 4, wherein said outer tube has a retainer for engaging and preventing said inner tube from dropping off said outer tube when said inner tube is moved most forwardly.

8. An endoscopic instrument according to claim 4, wherein each of said resilient ring-shaped members comprises an O-ring of rubber.

9. An endoscopic instrument according to claim 3, or further comprising a guide member disposed in said outer tube for guiding axial movement of said inner tube.

10. An endoscopic instrument according to claim 3, wherein said inner tube has a plurality of check surfaces behind said resilient ring-shaped members, respectively, for preventing the resilient ring-shaped members from being moved rearwardly when said rear slant surfaces abut against the resilient ring-shaped members in response to forward movement of said inner tube.

11. An endoscopic instrument according to claim 3, wherein said outer tube has a retainer for engaging and preventing said inner tube from dropping off said outer tube when said inner tube is moved most forwardly.

12. An endoscopic instrument according to claim 3, wherein each of said resilient ring-shaped members comprises an O-ring of rubber.

* * * * *